(12) United States Patent
Yamada et al.

(10) Patent No.: US 7,518,008 B2
(45) Date of Patent: Apr. 14, 2009

(54) PROCESSES FOR PRODUCING HAFNIUM COMPLEXES

(75) Inventors: Shuhei Yamada, Ube (JP); Atsushi Ryokawa, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/142,223

(22) Filed: Jun. 19, 2008

(65) Prior Publication Data

US 2009/0005584 A1     Jan. 1, 2009

(30) Foreign Application Priority Data

Jun. 26, 2007   (JP)  ............... 2007-167635
May 8, 2008   (JP)  ............... 2008-122073
May 19, 2008   (JP)  ............... 2008-131124

(51) Int. Cl.
*C07F 7/00*     (2006.01)
*C07C 49/92*     (2006.01)

(52) U.S. Cl. .......................... 556/40; 556/54

(58) Field of Classification Search ............ 556/40, 556/54
See application file for complete search history.

(56) References Cited

U.S. PATENT DOCUMENTS 7,319,158 B2    1/2008   Ryokawa et al.

OTHER PUBLICATIONS

J.C. Bailar Jr. et al, "Comprehensive Inorganic Chemistry", Pergamon Press Ltd. pp. 462-475 (1973).
R.C. Mehrotra, "Inorganic Chimica Acta Reviews", vol. 1, pp. 99-112 (1967).
Paul A Williams et al., "Novel Mononuclear Alkoxide Precursors for the MOCVD of $ZrO_2$ and $HfO_2$ Thin Films", Chemical Vapor Deposition, vol. 8, No. 4, pp. 163-170 (2002).

*Primary Examiner*—Porfirio Nazario Gonzalez
(74) *Attorney, Agent, or Firm*—Crowell & Moring LLP

(57) ABSTRACT

Disclosed are first to sixth processes for respectively producing hafnium tetra-tertiary-butoxide, tetrakis(acetylacetonato) hafnium, tetrakis(1-methoxy-2-methyl-2-propanolato) hafnium, hafnium tetra-tertiary-amyloxide, tetrakis(3-methyl-3-pentoxy)hafnium, and tetrakis (hexafluoroacetylacetonato)hafnium. The first process includes the steps of (a) adding a compound $A(O_yXO_nRf)_m$ (e.g., $CF_3SO_3H$) to a crude hafnium amide $Hf[N(R_1)(R_2)]_4$; (b) subjecting a product of the step (a) to a distillation under reduced pressure; (c) adding a lithium alkylamide $Li(NR_3R_4)$ to a fraction obtained by the step (b); (d) subjecting a product of the step (c) to a distillation under reduced pressure; (e) adding tertiary butanol to a fraction obtained by the step (d); and (f) subjecting a product of the step (e) to a distillation under reduced pressure. The tertiary butanol of the step (e) is replaced with acetylacetone, 1-methoxy-2-methyl-2-propanol, tertiary amyl alcohol, 3-methyl-3-pentanol, and hexafluoroacetylacetone in the second to six processes, respectively.

12 Claims, No Drawings

US 7,518,008 B2

PROCESSES FOR PRODUCING HAFNIUM COMPLEXES

BACKGROUND OF THE INVENTION

The present invention relates to processes for producing hafnium tetra-tertiary-butoxide $Hf(OC_4H_9)_4$, tetrakis(acetylacetonato)hafnium $Hf(C_5H_7O_2)_4$, tetrakis(1-methoxy-2-methyl-2-propanolato)hafnium $Hf(C_5H_{11}O_2)_4$, hafnium tetra-tertiary-amyloxide $Hf(OC_5H_{11})_4$, tetrakis(3-methyl-3-pentoxy)hafnium $Hf(OC_6H_{13})_4$, and tetrakis(hexafluoroacetylacetonato)hafnium $Hf(C_5F_6HO_2)_4$, which are regarded as promising hafnium film-forming materials of hafnium-series insulating films (e.g., $HfO_2$ and HfSiON), which attract much attention as the next generation high dielectric constant gate insulating films in semiconductor production.

Hitherto, $SiO_2$ has been used for a long time for gate insulating films in semiconductor production. This is because it was possible to respond to the trend toward finer devices along with higher integration of semiconductors by making $SiO_2$ films thinner. In recent years, however, the trend toward finer devices has grown further in order to achieve higher functionality and higher integration of LSI. As a result, physical limit is getting closer in making $SiO_2$ films thinner, and it is now difficult to respond to the trend toward further finer devices. Thus, hafnium-series insulating films attract much attention as gate insulating films that are substitutes for $SiO_2$ films. Hafnium-series insulating films have dielectric constants several times higher than that of $SiO_2$, and it is possible for that to increase the physical film thickness. Therefore, hafnium-series materials are those capable of responding to the trend toward finer devices.

To form such hafnium-series insulating films, it is possible to cite physical vapor deposition (PVD) and chemical vapor deposition (CVD). In general, it is difficult in PVD to form a uniform film on an uneven substrate and to control the film composition. In CVD, however, it is possible to form a uniform film on substrate irrespective of whether the substrate has unevenness or not, and it is superior in controlling the film composition. In forming gate insulating films, it may be necessary to form a uniform film on an uneven portion, although it may depend on the process of the gate stack production. Furthermore, it is important to control the film composition, since the film composition affects electric characteristics of semiconductor. Therefore, it is a current mainstream to use CVD for forming gate insulating films.

It is necessary to provide a hafnium film-forming raw material that has a high vapor pressure in order to form a hafnium-series insulating film by CVD. As a hafnium complex that is a hafnium film-forming raw material that has a high vapor pressure, it is necessary to have a bulky substituent in order to prevent the bonding intermolecular interaction (e.g., crosslinking coordinate bond) and to have a small molecular weight. As hafnium film-forming materials that have such necessities and attract attention in recent years, there are hafnium complexes such as hafnium tetra-tertiary-butoxide $Hf(OC_4H_9)_4$, tetrakis(acetylacetonato)hafnium $Hf(C_5H_7O_2)_4$, tetrakis(1-methoxy-2-methyl-2-propanolato)hafnium $Hf(C_5H_{11}O_2)_4$, hafnium tetra-tertiary-amyloxide $Hf(OC_5H_{11})_4$, tetrakis(3-methyl-3-pentoxy)hafnium $Hf(OC_6H_{13})_4$, and tetrakis(hexafluoroacetylacetonato)hafnium $Hf(C_5F_6HO_2)_4$. These six hafnium complexes respectively have relatively high vapor pressures of 90° C./6.5 Torr, 82° C./0.001 Torr, 135° C./7.6 Torr, 125° C./3 Torr, 65° C./0.3 Torr and 120° C./0.15 Torr and therefore are materials capable of becoming CVD film-forming materials for hafnium-series insulating films. The gate insulating film is positioned at a bottom portion of a semiconductor device, and the gate insulating film of the next-generation semiconductors becomes an ultra thin film having a film thickness of several nanometers. Thus, impurities in the gate insulating film have an extremely large influence on the electric characteristics of semiconductors. Therefore, a hafnium film-forming raw material therefor is required to be a high-purity product having an extremely low impurity concentration.

It is known to produce hafnium tetra-tertiary-butoxide $Hf(OC_4H_9)_4$, tetrakis(acetylacetonato)hafnium $Hf(C_5H_7O_2)_4$, tetrakis(1-methoxy-2-methyl-2-propanolato)hafnium $Hf(C_5H_{11}O_2)_4$, hafnium tetra-tertiary-amyloxide $Hf(OC_5H_{11})_4$, tetrakis(3-methyl-3-pentoxy)hafnium $Hf(OC_6H_{13})_4$, or tetrakis(hexafluoroacetylacetonato)hafnium $Hf(C_5F_6HO_2)_4$ by obtaining a hafnium amide from hafnium tetrachloride and lithium alkylamide as starting materials and then reacting the hafnium amide with tertiary butanol $C_4H_{10}O$, acetylacetone $C_5H_8O_2$, 1-methoxy-2-methyl-2-propanol $C_5H_{12}O_2$, tertiary amyl alcohol $C_5H_{12}O$, 3-methyl-3-pentanol $C_6H_{14}O$, or hexafluoroacetylacetone $C_5F_6H_2O_2$ (see J. C. Bailar, H. J. Emeleus, Sir Ronald Nyholm, and A. F. Trotman-Dickenson, "Comprehensive Inorganic Chemistry", Pergamon Press Ltd. pp. 462-475 (1973); R. C. Mehrotra, "Inorganic Chimica Acta Reviews", Vol. 1, pp. 99-112 (1967); and Paul A. Williams, John L. Roberts, Anthony C. Jones, et al., "Chem. Vap. Deposition", Vol. 8, pp. 163-170 (2002)).

SUMMARY OF THE INVENTION

It is an object of the present invention to provide a process for producing hafnium tetra-tertiary-butoxide $Hf(OC_4H_9)_4$, tetrakis(acetylacetonato)hafnium $Hf(C_5H_7O_2)_4$, tetrakis(1-methoxy-2-methyl-2-propanolato)hafnium $Hf(C_5H_{11}O_2)_4$, hafnium tetra-tertiary-amyloxide $Hf(OC_5H_{11})_4$, tetrakis(3-methyl-3-pentoxy)hafnium $Hf(OC_6H_{13})_4$, or tetrakis(hexafluoroacetylacetonato)hafnium $Hf(C_5F_6HO_2)_4$ with high yield, from which a zirconium component has easily and safely been removed, and which can be used in semiconductor field.

According to the present invention, there is provided a first process for producing hafnium tetra-tertiary-butoxide $Hf(OC_4H_9)_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding tertiary butanol $C_4H_{10}O$ to a fraction obtained by the step (d); and (f) subjecting a product of the step (e) to a distillation under reduced pressure.

According to the present invention, there is provided a second process for producing tetrakis(acetylacetonato) hafnium $Hf(C_5H_7O_2)_4$. The second process is the same as the first process, except that acetylacetone $C_5H_8O_2$ is used in the step (e) in place of the tertiary butanol $C_4H_{10}O$.

According to the present invention, there is provided a third process for producing tetrakis(1-methoxy-2-methyl-2-propanolato)hafnium $Hf(C_5H_{11}O_2)_4$. The third process is the same as the first process, except that 1-methoxy-2-methyl-2-propanol $C_5H_{12}O_2$ is used in the step (e) in place of the tertiary butanol $C_4H_{10}O$.

According to the present invention, there is provided a fourth process for producing hafnium tetra-tertiary-amyloxide $Hf(OC_5H_{11})_4$. The fourth process is the same as the first process, except that tertiary amyl alcohol $C_5H_{12}O$ is used in the step (e) in place of the tertiary butanol $C_4H_{10}O$.

According to the present invention, there is provided a fifth process for producing tetrakis(3-methyl-3-pentoxy)hafnium $Hf(OC_6H_{13})_4$. The fifth process is the same as the first process, except that 3-methyl-3-pentanol $C_6H_{14}O$ is used in the step (e) in place of the tertiary butanol $C_4H_{10}O$.

According to the present invention, there is provided a sixth process for producing tetrakis(hexafluoroacetylacetonato)hafnium $Hf(C_5F_6HO_2)_4$. The sixth process is the same as the first process, except that hexafluoroacetylacetone $C_5F_6H_2O_2$ is used in the step (e) in place of the tertiary butanol $C_4H_{10}O$.

It is possible by the first to sixth processes to produce hafnium tetra-tertiary-butoxide $Hf(OC_4H_9)_4$, tetrakis(acetylacetonato)hafnium $Hf(C_5H_7O_2)_4$, tetrakis(1-methoxy-2-methyl-2-propanolato)hafnium $Hf(C_5H_{11}O_2)_4$, hafnium tetra-tertiary-amyloxide $Hf(OC_5H_{11})_4$, tetrakis(3-methyl-3-pentoxy)hafnium $Hf(OC_6H_{13})_4$, and tetrakis(hexafluoroacetylacetonato)hafnium $Hf(C_5F_6HO_2)_4$ with high yield, in which the amount of the zirconium impurity has been reduced to a level necessary for semiconductor film-forming materials. Therefore, the target product can be used for uses in which high-purity is required. For example, it can be used as a CVD film-forming raw material for forming high dielectric-constant gate insulating films in semiconductor production processes. According to need, in the first to six processes, it is optional to repeat the step (a) by adding the compound $A(O_yXO_nRf)_m$ of the step (a) to the product of the step (b), prior to conducting the steps (c) to (f), for example, as shown in Example 1. With this, it becomes possible to further reduce the zirconium content of the target product.

DETAILED DESCRIPTION

It is possible by the first to six processes to obtain the target product, in which zirconium content has been reduced to 100 wtppm or less, preferably 10 wtppm or less, more preferably 1 wtppm or less, from the crude hafnium amide of the step (a), in which zirconium content is 1-30,000 wtppm.

The steps (a) and (b) of the first to sixth processes are conducted for the purpose of removing zirconium impurities from the crude hafnium amide. In fact, the initial zirconium content of 1-30,000 wtppm of the crude hafnium amide used in the step (a) can be reduced by about 1/10 to about 9/10 in a fraction (containing the hafnium amide as a main component) obtained by the step (b). In contrast, zirconium concentration in the bottom residue after the step (b) increases. With this, it is assumed that zirconium impurities (e.g., zirconium amide) in the crude hafnium amide are turned by the step (a) to nonvolatile substances having low vapor pressures.

Examples of the crude hafnium amide represented by the formula of $Hf[N(R_1)(R_2)]_4$ include tetrakis(diethylamido) hafnium $Hf[N(C_2H_5)_2]_4$ and tetrakis(dimethylamido) hafnium $Hf[N(CH_3)_2]_4$.

According to the above definition, the compound represented by the formula of $A(O_yXO_nRf)_m$, which is used in the step (a), is selected from $RfCOOH$, $RfSO_3H$, $(RfCO)_2O$, $(RfSO_2)_2O$, and $Hf(RfSO_3)_4$. Examples of this compound include acetic acid, trifluoroacetic acid, benzoic acid, methanesulfonic acid, trifluoromethanesulfonic acid, benzenesulfonic acid acetic anhydride, trifluoroacetic anhydride, benzoic anhydride, methanesulfonic anhydride, trifluoromethanesulfonic anhydride, benzenesulfonic anhydride, and hafnium trifluoromethanesulfonato. Of these, trifluoromethanesulfonic acid is preferable, which has a low price and a large advantageous effect.

The compound $A(O_yXO_nRf)_m$ may be added in an amount of 1-100 moles, relative to 1 mol of zirconium component of the hafnium amide. It is preferably 5-50 moles, from the viewpoint of suppressing side reactions with the hafnium amide.

Since a vigorous heat generation occurs during the step (a), the reaction temperature of the step (a) may be −78 to 100° C., preferably −78 to 30° C., from the viewpoint of suppressing side reactions.

It is preferable to conduct a stirring for 1 to 3 hours between the steps (a) and (b) from the viewpoint of homogenizing the reaction solution.

The step (b) may be conducted by normal method preferably under a reduced pressure of 0.0001 to 0.02 kPa. The addition of the compound $A(O_yXO_nRf)_m$ in the step (a) causes a vapor pressure difference between zirconium component and hafnium component. Therefore, it is possible by a simple distillation under reduced pressure of the step (b) to easily obtain a fraction, which contains the hafnium amide as a major component and in which the amount of zirconium component has been reduced.

The steps (c) and (d) are conducted for the purpose of removing the compound $A(O_yXO_nRf)_m$ (i.e., a carbonyl or sulfonyl component) from the fraction obtained by the step (b). In fact, the fraction obtained by the step (b) may contain about 0.1 to 4 wt % of the carbonyl or sulfonyl component.

In the step (c), the carbonyl or sulfonyl component in the hafnium amide is turned into a nonvolatile compound (e.g., lithium perfluoroalkylsulfonate) by adding the lithium alkylamide. Then, the hafnium amide is isolated by conducting a distillation under reduced pressure in the step (d). With this, the carbonyl or sulfonyl component concentration in the resulting fraction can be reduced to less than the detection limit (10 wtppm) of ion chromatogram. The zirconium concentration in the hafnium amide does almost not change before and after the removal of the carbonyl or sulfonyl component (i.e., the steps (c) and (d)).

Examples of lithium alkylamide Li(NR$_3$R$_4$) of the step (c) include lithium dimethylamide, lithium ethylmethylamide, and lithium diethylamide. In the step (c), a lithium alkylamide having a substituent that is the same as the ligand of the hafnium amide is used. For example, in case that the hafnium amide is tetrakis(diethylamido)hafnium, lithium diethylamide is used in the step (c). Furthermore, in case that the hafnium amide is tetrakis(dimethylamido)hafnium, lithium dimethylamide is used in the step (c).

The amount of lithium alkylamide is preferably 1-50 equivalents relative to 1 equivalent of the carbonyl or sulfonyl component contained in the fraction obtained by the step (b). If it is less than 1 equivalent, the removal of the carbonyl or sulfonyl component may become insufficient. Even if it is greater than 50 equivalents, it is not expected to have a further reduction of the carbonyl or sulfonyl component. Furthermore, it is not economical.

Lithium alkylamide is in solid (powder) at 25° C. It is possible to add lithium alkylamide itself in solid to the fraction obtained by the step (b). Alternatively, it is possible to previously dissolve lithium alkylamide in an organic solvent and then add the resulting solution to the fraction obtained by the step (b). Examples of this organic solvent include diethyl ether, hexane, and toluene, in view of dissolution, reactivity, etc of the hafnium amide. In particular, toluene is preferable due to its availability and low price.

It is possible to conduct the step (c) at a temperature of -78 to 200° C., preferably 0-100° C. A temperature higher than 200° C. is not preferable, since lithium alkylamide may be decomposed by heat. Immediately after the step (c), the step (d) may be conducted to isolate the hafnium amide. Alternatively, stirring may be conducted, prior to the step (d).

The step (d) may be conducted by normal distillation preferably under a reduced pressure of 0.0001-0.02 kPa. It is possible by the step (d) to obtain the hafnium amide in which the content of the carbonyl or sulfonyl component is 10 wtppm or less.

The steps (e) and (f) of the first process are conducted for producing hafnium tetra-tertiary-butoxide Hf(OC$_4$H$_9$)$_4$ from the purified hafnium amide obtained by the step (d). Those of the second process are for producing tetrakis(acetylacetonato)hafnium Hf(C$_5$H$_7$O$_2$)$_4$ therefrom, those of the third process are for producing tetrakis(1-methoxy-2-methyl-2-propanolato)hafnium Hf(C$_5$H$_{11}$O$_2$)$_4$ therefrom, those of the fourth process are for producing hafnium tetra-tertiary-amyloxide Hf(OC$_5$H$_{11}$)$_4$ therefrom, those of the fifth process are for producing tetrakis(3-methyl-3-pentoxy)hafnium Hf(OC$_6$H$_{13}$)$_4$ therefrom, and those of the six process for producing tetrakis(hexafluoroacetylacetonato)hafnium Hf(C$_5$F$_6$HO$_2$)$_4$ therefrom.

In fact, the reaction (ligand exchange reaction) of the step (e) of the first process can be expressed as follows.

Hf[N(R$_1$)(R$_2$)]$_4$ + 4C$_4$H$_{10}$O  Hf(OC$_4$H$_9$)$_4$ + 4NH(R$_1$)(R$_2$)
                      tert-butanol                                   dialkylamine Similarly, that of the second process can be expressed as follows.

Hf[N(R$_1$)(R$_2$)]$_4$ + 4C$_5$H$_8$O$_2$ 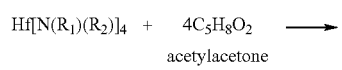
                      acetylacetone -continued
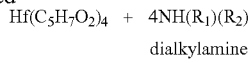
Hf(C$_5$H$_7$O$_2$)$_4$ + 4NH(R$_1$)(R$_2$)
                        dialkylamine Similarly, that of the third process can be expressed as follows.

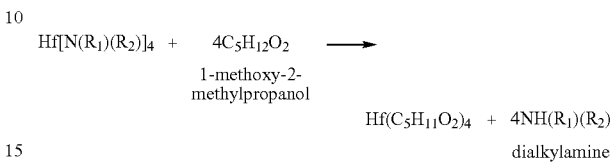

Similarly, that of the fourth process can be expressed as follows.

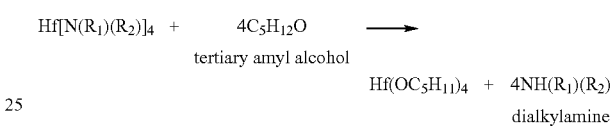

Similarly, that of the fifth process can be expressed as follows.

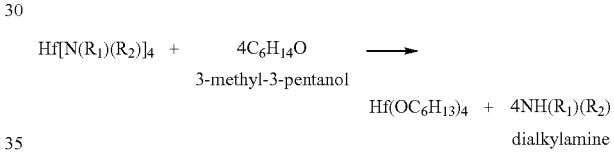

Similarly, that of the sixth process can be expressed as follows.

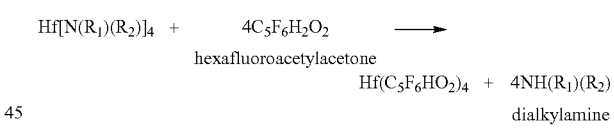

In each of the first to sixth processes, the vapor pressure difference between the target product (i.e., each of hafnium tetra-tertiary-butoxide Hf(OC$_4$H$_9$)$_4$, tetrakis(acetylacetonato)hafnium Hf(C$_5$H$_7$O$_2$)$_4$, tetrakis(1-methoxy-2-methyl-2-propanolato)hafnium Hf(C$_5$H$_{11}$O$_2$)$_4$, hafnium tetra-tertiary-amyloxide Hf(OC$_5$H$_{11}$)$_4$, tetrakis(3-methyl-3-pentoxy)hafnium Hf(OC$_6$H$_{13}$)$_4$, and tetrakis(hexafluoroacetylacetonato)hafnium Hf(C$_5$F$_6$HO$_2$)$_4$) and the dialkylamine is very large. Therefore, it is possible to sufficiently and easily isolate the target product by conducting a simple distillation under reduced pressure in the step (f).

The zirconium concentration of the target product obtained by the step (f) is almost the same as that of the fraction obtained by the step (d).

In the step (e) of the first to sixth processes, the reactant (i.e., tertiary butanol, acetylacetone, 1-methoxy-2-methyl-2-propanol, tertiary amyl alcohol, 3-methyl-3-pentanol, or hexafluoroacetylacetone) is added in an amount of 4 to 8moles relative to 1 mol of the hafnium amide. If it is less than 4 moles, yield of the target product may decrease accordingly.

If it is greater than 8 moles, the effect of adding the reactant may not be improved further. Furthermore, it is not economical.

Since a vigorous heat generation occurs in each step (e) of the first to sixth processes, the reaction may be conducted at a temperature of −78 to 100° C., preferably −78 to 30° C., from the viewpoint of suppressing side reactions. It is preferable to conduct stirring for 1 to 3 hours between the steps (e) and (f) in the first to sixth processes from the viewpoint of conducting the reaction sufficiently.

The step (f) of the first to sixth processes may be conducted by normal distillation preferably under a reduced pressure of 0.0001 to 0.02 kPa.

The following nonlimitative examples are illustrative of the present invention.

EXAMPLE 1

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 15.6 g (104 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 66.5 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 138 wtppm. It was found by ion chromatography that trifluoromethanesulfonic acid ion concentration of the fraction was 2.1 wt %. A bottom residue after the distillation was in 35.0 g and had a zirconium concentration of 1,884 wtppm and a trifluoromethanesulfonic acid ion concentration of 29.0 wt %.

Then, 65 g of the obtained fraction was put into a 500 mL, five-necked, glass flask equipped with a dropping funnel, a reflux condenser, a thermometer and a stirrer, followed by cooling to 0° C. and then adding 10.1 g (67 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.3 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 19 wtppm. It was found by ion chromatography that trifluoromethanesulfonic acid ion concentration of the fraction was 2.0 wt %. A bottom residue after the distillation was in 22.8 g and had a zirconium concentration of 355 wtppm and a trifluoromethanesulfonic acid ion concentration of 45.1 wt %.

Then, 40.0 g of the obtained fraction was put into a 500 mL, five-necked, glass flask equipped with a reflux condenser, a thermometer and a stirrer, followed by adding 1.0 g (13 mmol) of lithium diethylamide $LiN(C_2H_5)_2$ and then stirring at 25° C. for 1 hr. Then, this reaction solution was distilled under a condition of 125° C. and 0.12 kPa, thereby obtaining 38.8 g of a fraction. The obtained fraction was found by $^1HNMR$ to be tetrakis(diethylamido)hafnium $Hf[N(C_2H_5)_2]_4$. Zirconium concentration of the fraction was 19 wtppm, and trifluoromethanesulfonic acid ion concentration of the fraction was less than 10 wtppm (detection limit). A bottom residue after the distillation was in 2.0 g and had a zirconium concentration of 30 wtppm and a trifluoromethanesulfonic acid ion concentration of 6.8 wt %.

Then, 30.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 38.1 g (514 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 29.7 g of a fraction. The obtained fraction was found by $^1HNMR$ to be hafnium tetra-tertiary-butoxide $Hf(OC_4H_9)_4$. It was found by an ICP atomic emission spectrometer that zirconium concentration of the fraction was 19 wtppm. Yield from the initial tetrakis(diethylamido)hafnium (zirconium concentration: 1,000 wtppm) was 42 wt %.

EXAMPLE 2

A 500 mL, five-necked, glass flask was equipped with a powder dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 20.0 g (25.8 mmol) of hafnium trifluoromethanesulfonato $Hf(CF_3SO_3)_4$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 79.5 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 198 wtppm. It was found by ion chromatography that trifluoromethanesulfonic acid ion concentration of the fraction was 4.2 wt %. A bottom residue after the distillation was in 31.0 g and had a zirconium concentration of 2,840 wtppm and a trifluoromethanesulfonic acid ion concentration of 28.8 wt %.

Then, 75.0 g of the obtained fraction was put into a 500 mL, five-necked, glass flask equipped with a powder dropping funnel, a reflux condenser, a thermometer and a stirrer, followed by cooling to 0° C. and then adding 1.8 g (2 mmol) of hafnium trifluoromethanesulfonato $Hf(CF_3SO_3)_4$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 63.9 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 61 wtppm. It was found by ion chromatography that trifluoromethanesulfonic acid ion concentration of the fraction was 1.8 wt %. A bottom residue after the distillation was in 8.7 g and had a zirconium concentration of 1,200 wtppm and a trifluoromethanesulfonic acid ion concentration of 17.0 wt %.

Then, 60.0 g of the obtained fraction was put into a 500 mL, five-necked, glass flask equipped with a reflux condenser, a thermometer and a stirrer, followed by adding 4.7 g (59 mmol) of lithium diethylamide $LiN(C_2H_5)_2$ and then stirring at 25° C. for 1 hr. Then, this reaction solution was distilled under a condition of 125° C. and 0.12 kPa, thereby obtaining 55.0 g of a fraction. The obtained fraction was found by $^1$HNMR to be tetrakis(diethylamido)hafnium $Hf[N(C_2H_5)_2]_4$. Zirconium concentration of the fraction was 48 wtppm, and trifluoromethanesulfonic acid ion concentration of the fraction was less than 10 wtppm (detection limit). A bottom residue after the distillation was in 3.5 g and had a zirconium concentration of 291 wtppm and a trifluoromethanesulfonic acid ion concentration of 28.5 wt %.

Then, 50.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 63.5 g (857 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 49.3 g of a fraction. The obtained fraction was found by $^1$HNMR to be hafnium tetra-tertiary-butoxide $Hf(OC_4H_9)_4$. It was found by an ICP atomic emission spectrometer that zirconium concentration of the fraction was 46 wtppm. Yield from the initial tetrakis (diethylamido)hafnium (zirconium concentration: 1,000 wtppm) was 60 wt %.

EXAMPLE 3

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 733 wtppm of zirconium, followed by cooling to 0° C. and then adding 29.5 g (104 mmol) of trifluoromethanesulfonic anhydride $(CF_3SO_2)_2O$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 69.5 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 80 wtppm. It was found by ion chromatography that trifluoromethanesulfonic acid ion concentration of the fraction was 2.4 wt %. A bottom residue after the distillation was in 31.7 g and had a zirconium concentration of 2,112 wtppm and a trifluoromethanesulfonic acid ion concentration of 33.8 wt %.

Then, 65.0 g of the obtained fraction was put into a 500 mL, five-necked, glass flask equipped with a reflux condenser, a thermometer and a stirrer, followed by adding 8.8 g (111 mmol) of lithium diethylamide $LiN(C_2H_5)_2$ and then stirring at 25° C. for 1 hr. Then, this reaction solution was distilled under a condition of 125° C. and 0.12 kPa, thereby obtaining 49.0 g of a fraction. The obtained fraction was found by $^1$HNMR to be tetrakis(diethylamido)hafnium $Hf[N(C_2H_5)_2]_4$. Zirconium concentration of the fraction was 66 wtppm, and trifluoromethanesulfonic acid ion concentration of the fraction was less than 10 wtppm (detection limit). A bottom residue after the distillation was in 7.5 g and had a zirconium concentration of 147 wtppm and a trifluoromethanesulfonic acid ion concentration of 16.7 wt %.

Then, 45.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 57.1 g (772 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 44.5 g of a fraction. The obtained fraction was found by $^1$HNMR to be hafnium tetra-tertiary-butoxide $Hf(OC_4H_9)_4$. It was found by an ICP atomic emission spectrometer that zirconium concentration of the fraction was 65 wtppm. Yield from the initial tetrakis (diethylamido)hafnium (zirconium concentration: 733 wtppm) was 51 wt %.

EXAMPLE 4

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 733 wtppm of zirconium, followed by cooling to 0° C. and then adding 11.9 g (104 mmol) of trifluoroacetic acid $CF_3CO_2H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 58.4 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 388 wtppm. It was found by ion chromatography that trifluoroacetic acid ion concentration of the fraction was 2.7 wt %. A bottom residue after the distillation was in 26.5 g and had a zirconium concentration of 1,786 wtppm and a trifluoroacetic acid ion concentration of 35.7 wt %.

Then, 55.0 g of the obtained fraction was put into a 500 mL, five-necked, glass flask equipped with a dropping funnel, a reflux condenser, a thermometer and a stirrer, followed by cooling to 0° C. and then adding 6.5 g (57 mmol) of trifluoroacetic acid $CF_3CO_2H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 32.1 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 205 wtppm. It was found by ion chromatography that trifluoroacetic acid ion concentration of the fraction was 2.8 wt %. A bottom residue after the distillation was in 14.6 g and had a zirconium concentration of 1,011 wtppm and a trifluoroacetic acid ion concentration of 48.6 wt %.

Then, 30.0 g of the obtained fraction was put into a 500 mL, five-necked, glass flask equipped with a dropping funnel, a reflux condenser, a thermometer and a stirrer, followed by cooling to 0° C. and then adding 3.6 g (31 mmol) of trifluoroacetic acid $CF_3CO_2H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 17.5 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 99 wtppm. It was found by ion chromatography that trifluoroacetic acid ion concentration of the fraction was 2.6 wt %. A bottom residue after the distillation was in 8.0 g and had a zirconium concentration of 534 wtppm and a trifluoroacetic acid ion concentration of 49.4 wt %.

Then, 15 g of the obtained fraction was put into a 500 mL, five-necked, glass flask equipped with a reflux condenser, a thermometer and a stirrer, followed by adding 0.6 g (8 mmol) of lithium diethylamide $LiN(C_2H_5)_2$ and then stirring at 25° C. for 1 hr. Then, this reaction solution was distilled under a condition of 125° C. and 0.12 kPa, thereby obtaining 13.4 g of a fraction. The obtained fraction was found by $^1HNMR$ to be tetrakis(diethylamido)hafnium $Hf[N(C_2H_5)_2]_4$. Zirconium concentration of the fraction was 93 wtppm, and trifluoroacetic acid ion concentration of the fraction was less than 10 wtppm (detection limit). A bottom residue after the distillation was in 1.0 g and had a zirconium concentration of 255 wtppm and a trifluoroacetic acid ion concentration of 44.0 wt %.

Then, 10.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 12.7 g (171 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 9.9 g of a fraction. The obtained fraction was found by $^1HNMR$ to be hafnium tetra-tertiary-butoxide $Hf(OC_4H_9)_4$. It was found by an ICP atomic emission spectrometer that zirconium concentration of the fraction was 91 wtppm. Yield from the initial tetrakis(diethylamido)hafnium (zirconium concentration: 733 wtppm) was 17 wt %.

EXAMPLE 5

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 733 wtppm of zirconium, followed by cooling to 0° C. and then adding 10.0 g (104 mmol) of methanesulfonic acid $CH_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 67.2 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 258 wtppm. It was found by ion chromatography that methanesulfonic acid ion concentration of the fraction was 2.5 wt %. A bottom residue after the distillation was in 27.0 g and had a zirconium concentration of 2,003 wtppm and a methanesulfonic acid ion concentration of 30.6 wt %.

Then, 65.0 g of the obtained fraction was put into a 500 mL, five-necked, glass flask equipped with a dropping funnel, a reflux condenser, a thermometer and a stirrer, followed by cooling to 0° C. and then adding 6.5 g (68 mmol) of methanesulfonic acid $CH_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.7 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 91 wtppm. It was found by ion chromatography that methanesulfonic acid ion concentration of the fraction was 2.6 wt %. A bottom residue after the distillation was in 17.6 g and had a zirconium concentration of 730 wtppm and a methanesulfonic acid ion concentration of 39.7 wt %.

Then, 40.0 g of the obtained fraction was put into a 500 mL, five-necked, glass flask equipped with a reflux condenser, a thermometer and a stirrer, followed by adding 1.7 g (21.5 mmol) of lithium diethylamide $LiN(C_2H_5)_2$ and then stirring at 25° C. for 1 hr. Then, this reaction solution was distilled under a condition of 125° C. and 0.12 kPa, thereby obtaining 30.2 g of a fraction. The obtained fraction was found by $^1HNMR$ to be tetrakis(diethylamido)hafnium $Hf[N(C_2H_5)_2]_4$. Zirconium concentration of the fraction was 86 wtppm, and methanesulfonic acid ion concentration of the fraction was less than 10 wtppm (detection limit). A bottom residue after the distillation was in 2.5 g and had a zirconium concentration of 410 wtppm and a methanesulfonic acid ion concentration of 42.3 wt %.

Then, 25.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 31.8 g (429 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 24.8 g of a fraction. The obtained fraction was found by $^1HNMR$ to be hafnium tetra-tertiary-butoxide $Hf(OC_4H_9)_4$. It was found by an ICP atomic emission spectrometer that zirconium concentration of the fraction was 85 wtppm. Yield from the initial tetrakis (diethylamido)hafnium (zirconium concentration: 733 wtppm) was 33 wt %.

EXAMPLE 6

A 500 mL, five-necked, glass flask was equipped with a powder dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 733 wtppm of zirconium, followed by cooling to 0° C. and then adding 16.5 g (104 mmol) of benzenesulfonic acid $C_6H_5SO_3H$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 70.5 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 341 wtppm. It was found by ion chromatography that benzenesulfonic acid ion concentration of the fraction was 0.1 wt %. A bottom residue after the distillation was in 34.0 g and had a zirconium concentration of 1,450 wtppm and a benzenesulfonic acid ion concentration of 47.4 wt %.

Then, 65.0 g of the obtained fraction was put into a 500 mL, five-necked, glass flask equipped with a powder dropping funnel, a reflux condenser, a thermometer and a stirrer, followed by cooling to 0° C. and then adding 10.7 g (67 mmol) of benzenesulfonic acid $C_6H_5SO_3H$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 45.8 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 158 wtppm. It was found by ion chromatography that benzenesulfonic acid ion concentration of the fraction was 0.2 wt %. A bottom residue after the distillation was in 22.1 g and had a zirconium concentration of 674 wtppm and a benzenesulfonic acid ion concentration of 48.5 wt %.

Then, 40.0 g of the obtained fraction was put into a 500 mL, five-necked, glass flask equipped with a powder dropping funnel, a reflux condenser, a thermometer and a stirrer, followed by cooling to 0° C. and then adding 6.6 g (41 mmol) of benzenesulfonic acid $C_6H_5SO_3H$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 28.2 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 74 wtppm. It was found by ion chromatography that benzenesulfonic acid ion concentration of the fraction was 0.1 wt %. A bottom residue after the distillation was in 13.6 g and had a zirconium concentration of 313 wtppm and a benzenesulfonic acid ion concentration of 48.6 wt %.

Then, 25.0 g of the obtained fraction was put into a 500 mL, five-necked, glass flask equipped with a reflux condenser, a thermometer and a stirrer, followed by adding 0.1 g (1 mmol) of lithium diethylamide $LiN(C_2H_5)_2$ and then stirring at 25° C. for 1 hr. Then, this reaction solution was distilled under a condition of 125° C. and 0.12 kPa, thereby obtaining 24.0 g of a fraction. The obtained fraction was found by $^1$HNMR to be tetrakis(diethylamido)hafnium $Hf[N(C_2H_5)_2]_4$. Zirconium concentration of the fraction was 72 wtppm, and benzenesulfonic acid ion concentration of the fraction was less than 10 wtppm (detection limit). A bottom residue after the distillation was in 0.7 g and had a zirconium concentration of 147 wtppm and a benzenesulfonic acid ion concentration of 3.6 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 25.4 g (343 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 19.9 g of a fraction. The obtained fraction was found by $^1$HNMR to be hafnium tetra-tertiary-butoxide $Hf(OC_4H_9)_4$. It was found by an ICP atomic emission spectrometer that zirconium concentration of the fraction was 70 wtppm. Yield from the initial tetrakis (diethylamido)hafnium (zirconium concentration: 733 wtppm) was 33 wt %.

EXAMPLE 7

A 500 mL, five-necked, glass flask was equipped with a powder dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 18.0 g (104 mmol) of methanesulfonic anhydride $(CH_3SO_2)_2O$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 69.0 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 195 wtppm. It was found by ion chromatography that methanesulfonic acid ion concentration of the fraction was 1.7 wt %. A bottom residue after the distillation was in 35.0 g and had a zirconium concentration of 2,471 wtppm and a methanesulfonic acid ion concentration of 25.0 wt %.

Then, 65.0 g of the obtained fraction was put into a 500 mL, five-necked, glass flask equipped with a powder dropping funnel, a reflux condenser, a thermometer and a stirrer, followed by cooling to 0° C. and then adding 11.7 g (68 mmol) of methanesulfonic anhydride $(CH_3SO_2)_2O$ from the powder dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 44.8 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 38 wtppm. It was found by ion chromatography that methanesulfonic acid ion concentration of the fraction was 1.6 wt %. A bottom residue after the distillation was in 22.8 g and had a zirconium concentration of 483 wtppm and a methanesulfonic acid ion concentration of 52.4 wt %.

Then, 40.0 g of the obtained fraction was put into a 500 mL, five-necked, glass flask equipped with a reflux condenser, a thermometer and a stirrer, followed by adding 1.1 g (13.9 mmol) of lithium diethylamide $LiN(C_2H_5)_2$ and then stirring at 25° C. for 1 hr. Then, this reaction solution was distilled under a condition of 125° C. and 0.12 kPa, thereby obtaining 38.3 g of a fraction. The obtained fraction was found by $^1$HNMR to be tetrakis(diethylamido)hafnium $Hf[N(C_2H_5)_2]_4$. Zirconium concentration of the fraction was 36 wtppm, and methanesulfonic acid ion concentration of the fraction was less than 10 wtppm (detection limit). A bottom residue after the distillation was in 1.1 g and had a zirconium concentration of 117 wtppm and a methanesulfonic acid ion concentration of 55.1 wt %.

Then, 35.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 44.4 g (600 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 34.7 g of a fraction. The obtained fraction was found by $^1$HNMR to be hafnium tetra-tertiary-butoxide Hf(OC$_4$H$_9$)$_4$. It was found by an ICP atomic emission spectrometer that zirconium concentration of the fraction was 35 wtppm. Yield from the initial tetrakis (diethylamido)hafnium (zirconium concentration: 1,000 wtppm) was 45 wt %.

EXAMPLE 8

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium Hf[N(C$_2$H$_5$)$_2$]$_4$ containing 900 wtppm of zirconium, followed by cooling to 0° C. and then adding 3.5 g (23 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 95.8 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 492 wtppm. It was found by ion chromatography that trifluoromethanesulfonic acid ion concentration of the fraction was 1.6 wt %. A bottom residue after the distillation was in 6.5 g and had a zirconium concentration of 6,591 wtppm and a trifluoromethanesulfonic acid ion concentration of 28.5 wt %.

Then, 90.0 g of the obtained fraction was put into a 500 mL, five-necked, glass flask equipped with a dropping funnel, a reflux condenser, a thermometer and a stirrer, followed by cooling to 0° C. and then adding 3.1 g (21 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 83.9 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 163 wtppm. It was found by ion chromatography that trifluoromethanesulfonic acid ion concentration of the fraction was 1.7 wt %. A bottom residue after the distillation was in 7.2 g and had a zirconium concentration of 4,250 wtppm and a trifluoromethanesulfonic acid ion concentration of 41.1 wt %.

Then, 80.0 g of the obtained fraction was put into a 500 mL, five-necked, glass flask equipped with a dropping funnel, a reflux condenser, a thermometer and a stirrer, followed by cooling to 0° C. and then adding 2.8 g (19 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 71.4 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 48 wtppm. It was found by ion chromatography that trifluoromethanesulfonic acid ion concentration of the fraction was 1.4 wt %. A bottom residue after the distillation was in 9.6 g and had a zirconium concentration of 997 wtppm and a trifluoromethanesulfonic acid ion concentration of 31.5 wt %.

Then, 65.0 g of the obtained fraction was put into a 500 mL, five-necked, glass flask equipped with a dropping funnel, a reflux condenser, a thermometer and a stirrer, followed by cooling to 0° C. and then adding 2.3 g (15 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 60.2 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 20 wtppm. It was found by ion chromatography that trifluoromethanesulfonic acid ion concentration of the fraction was 1.5 wt %. A bottom residue after the distillation was in 4.6 g and had a zirconium concentration of 413 wtppm and a trifluoromethanesulfonic acid ion concentration of 47.3 wt %.

Then, 55.0 g of the obtained fraction was put into a 500 mL, five-necked, glass flask equipped with a dropping funnel, a reflux condenser, a thermometer and a stirrer, followed by cooling to 0° C. and then adding 2.0 g (13 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 49.7 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 6 wtppm. It was found by ion chromatography that trifluoromethanesulfonic acid ion concentration of the fraction was 1.6 wt %. A bottom residue after the distillation was in 5.7 g and had a zirconium concentration of 138 wtppm and a trifluoromethanesulfonic acid ion concentration of 33.2 wt %.

Then, 45.0 g of the obtained fraction was put into a 500 mL, five-necked, glass flask equipped with a dropping funnel, a reflux condenser, a thermometer and a stirrer, followed by cooling to 0° C. and then adding 1.6 g (11 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 40.5 g of a fraction. The obtained fraction was found by $^1$HNMR to contain tetrakis(diethylamido)hafnium Hf[N(C$_2$H$_5$)$_2$]$_4$ as a main component. It was found by an ICP atomic emission spectrometer that zirconium concentration of the fraction was 2 wtppm. It was found by ion chromatography that trifluoromethanesulfonic acid ion concentration of the fraction was 1.6 wt %. A bottom residue after the distillation was in 6.8 g and had a zirconium concentration of 27 wtppm and a trifluoromethanesulfonic acid ion concentration of 23.6 wt %.

Then, 35.0 g of the obtained fraction was put into a 500 mL, five-necked, glass flask equipped with a dropping funnel, a reflux condenser, a thermometer and a stirrer, followed by cooling to 0° C. and then adding 1.2 g (8 mmol) of trifluoromethanesulfonic acid CF$_3$SO$_3$H from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 31.1 g of a fraction.

The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 0.8 wtppm. It was found by ion chromatography that trifluoromethanesulfonic acid ion concentration of the fraction was 1.5 wt %. A bottom residue after the distillation was in 3.5 g and had a zirconium concentration of 11 wtppm and a trifluoromethanesulfonic acid ion concentration of 34.2 wt %.

Then, 25.0 g of the obtained fraction was put into a 500 mL, five-necked, glass flask equipped with a reflux condenser, a thermometer and a stirrer, followed by adding 1.0 g (13 mmol) of lithium diethylamide $LiN(C_2H_5)_2$ and then stirring at 25° C. for 1 hr. Then, this reaction solution was distilled under a condition of 125° C. and 0.12 kPa, thereby obtaining 24.5 g of a fraction. The obtained fraction was found by $^1$HNMR to be tetrakis(diethylamido)hafnium $Hf[N(C_2H_5)_2]_4$. Zirconium concentration of the fraction was 0.7 wtppm, and methanesulfonic acid ion concentration of the fraction was less than 10 wtppm (detection limit). A bottom residue after the distillation was in 1.3 g and had a zirconium concentration of 2.2 wtppm and a trifluoromethanesulfonic acid ion concentration of 13.2 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 25.3 g (343 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 19.8 g of a fraction. The obtained fraction was found by $^1$HNMR to be hafnium tetra-tertiary-butoxide $Hf(OC_4H_9)_4$. It was found by an ICP atomic emission spectrometer that zirconium concentration of the fraction was 0.6 wtppm. Yield from the initial tetrakis(diethylamido)hafnium (zirconium concentration: 900 wtppm) was 51 wt %.

EXAMPLE 9

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 15.6 g (104 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 66.5 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 138 wtppm. It was found by ion chromatography that trifluoromethanesulfonic acid ion concentration of the fraction was 2.1 wt %. A bottom residue after the distillation was in 35.0 g and had a zirconium concentration of 1,884 wtppm and a trifluoromethanesulfonic acid ion concentration of 29.0 wt %.

Then, 65 g of the obtained fraction was put into a 500 mL, five-necked, glass flask equipped with a dropping funnel, a reflux condenser, a thermometer and a stirrer, followed by cooling to 0° C. and then adding 10.1 g (67 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.3 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 19 wtppm. It was found by ion chromatography that trifluoromethanesulfonic acid ion concentration of the fraction was 2.0 wt %. A bottom residue after the distillation was in 22.8 g and had a zirconium concentration of 355 wtppm and a trifluoromethanesulfonic acid ion concentration of 45.1 wt %.

Then, 40.0 g of the obtained fraction was put into a 500 mL, five-necked, glass flask equipped with a reflux condenser, a thermometer and a stirrer, followed by adding 1.0 g (13 mmol) of lithium diethylamide $LiN(C_2H_5)_2$ and then stirring at 25° C. for 1 hr. Then, this reaction solution was distilled under a condition of 125° C. and 0.12 kPa, thereby obtaining 38.1 g of a fraction. The obtained fraction was found by $^1$HNMR to be tetrakis(diethylamido)hafnium $Hf[N(C_2H_5)_2]_4$. Zirconium concentration of the fraction was 16 wtppm, and trifluoromethanesulfonic acid ion concentration of the fraction was less than 10 wtppm (detection limit). A bottom residue after the distillation was in 1.7 g and had a zirconium concentration of 30 wtppm and a trifluoromethanesulfonic acid ion concentration of 6.8 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 34.3 g (343 mmol) of acetylacetone $C_5H_8O_2$ from the dropping funnel in dropwise manner by spending 1 hr. After the dropping, the temperature was increased to 20° C. with stirring for 1 hr.

This reaction solution was distilled under a condition of 82° C. and 0.13Pa, thereby obtaining 23.4 g of a fraction. The obtained fraction was found by $^1$HNMR to be tetrakis(acetylacetonato)hafnium $Hf(C_5H_7O_2)_4$. It was found by an ICP atomic emission spectrometer that zirconium concentration of the fraction was 16 wtppm. Yield from the initial tetrakis(diethylamido)hafnium (zirconium concentration: 1,000 wtppm) was 39 wt %.

EXAMPLE 10

A 500 mL, five-necked, glass flask was equipped with a dropping funnel, a reflux condenser, a thermometer and a stirrer, followed by replacing the inside atmosphere of the flask with nitrogen. This flask was charged with 200.0 g (428 mmol) of a tetrakis(diethylamido)hafnium $Hf[N(C_2H_5)_2]_4$ containing 1,000 wtppm of zirconium, followed by cooling to 0° C. and then adding 21.2 g (208 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 134.2 g of a fraction. The obtained fraction was found by $^1$HNMR to contain tetrakis(diethylamido)hafnium $Hf[N(C_2H_5)_2]_4$ as a main component. It was found by an ICP atomic emission spectrometer that zirconium concentration of the fraction was 137 wtppm. It was found by ion chromatography that trifluoromethanesulfonic acid ion concentration of the fraction was 2.0 wt %. A bottom residue after the distillation was in 68.5 g and had a zirconium concentration of 1,884 wtppm and a trifluoromethanesulfonic acid ion concentration of 29.0 wt %.

Then, 130 g of the obtained fraction was put into a 500 mL, five-necked, glass flask equipped with a dropping funnel, a reflux condenser, a thermometer and a stirrer, followed by cooling to 0° C. and then adding 20.1 g (134 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 86.9 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 18 wtppm. It was found by ion chromatography that trifluoromethanesulfonic acid ion concentration of the fraction was 2.1 wt %. A bottom residue after the distillation was in 45.4 g and had a zirconium concentration of 355 wtppm and a trifluoromethanesulfonic acid ion concentration of 46.3 wt %.

Then, 80.0 g of the obtained fraction was put into a 500 mL, five-necked, glass flask equipped with a reflux condenser, a thermometer and a stirrer, followed by adding 2.0 g (26 mmol) of lithium diethylamide $LiN(C_2H_5)_2$ and then stirring at 25° C. for 1 hr. Then, this reaction solution was distilled under a condition of 125° C. and 0.12 kPa, thereby obtaining 76.3 g of a fraction. The obtained fraction was found by $^1HNMR$ to be tetrakis(diethylamido)hafnium $Hf[N(C_2H_5)_2]_4$. Zirconium concentration of the fraction was 18 wtppm, and trifluoromethanesulfonic acid ion concentration of the fraction was less than 10 wtppm (detection limit). A bottom residue after the distillation was in 5.5 g and had a zirconium concentration of 30 wtppm and a trifluoromethanesulfonic acid ion concentration of 6.8 wt %.

Then, 70.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 93.6 g (900 mmol) of 1-methoxy-2-methyl-2-propanol $C_5H_{12}O_2$ from the dropping funnel in dropwise manner by spending 1 hr. After the dropping, the temperature was increased to 20° C. with stirring for 1 hr.

This reaction solution was distilled under a condition of 135° C. and 1.33 Pa, thereby obtaining 84.2 g of a fraction. The obtained fraction was found by $^1HNMR$ to be tetrakis(1-methoxy-2-methyl-2-propanolato)hafnium $Hf(C_5H_{11}O_2)_4$. It was found by an ICP atomic emission spectrometer that zirconium concentration of the fraction was 18 wtppm. Yield from the initial tetrakis(diethylamido)hafnium (zirconium concentration: 1,000 wtppm) was 41 wt %.

EXAMPLE 11

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 15.6 g (104 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 66.5 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 138 wtppm. It was found by ion chromatography that trifluoromethanesulfonic acid ion concentration of the fraction was 2.1 wt %. A bottom residue after the distillation was in 35.0 g and had a zirconium concentration of 1,884 wtppm and a trifluoromethanesulfonic acid ion concentration of 29.0 wt %.

Then, 65 g of the obtained fraction was put into a 500 mL, five-necked, glass flask equipped with a dropping funnel, a reflux condenser, a thermometer and a stirrer, followed by cooling to 0° C. and then adding 10.1 g (67 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.3 g of a fraction. The obtained fraction was found by $^1HNMR$ to contain tetrakis(diethylamido)hafnium $Hf[N(C_2H_5)_2]_4$ as a main component. It was found by an ICP atomic emission spectrometer that zirconium concentration of the fraction was 19 wtppm. It was found by ion chromatography that trifluoromethanesulfonic acid ion concentration of the fraction was 2.0 wt %. A bottom residue after the distillation was in 22.8 g and had a zirconium concentration of 355 wtppm and a trifluoromethanesulfonic acid ion concentration of 45.1 wt %.

Then, 40.0 g of the obtained fraction was put into a 500 mL, five-necked, glass flask equipped with a reflux condenser, a thermometer and a stirrer, followed by adding 1.0 g (13 mmol) of lithium diethylamide $LiN(C_2H_5)_2$ and then stirring at 25° C. for 1 hr. Then, this reaction solution was distilled under a condition of 125° C. and 0.12 kPa, thereby obtaining 38.1 g of a fraction. The obtained fraction was found by $^1HNMR$ to be tetrakis(diethylamido)hafnium $Hf[N(C_2H_5)_2]_4$. Zirconium concentration of the fraction was 16 wtppm, and trifluoromethanesulfonic acid ion concentration of the fraction was less than 10 wtppm (detection limit). A bottom residue after the distillation was in 1.7 g and had a zirconium concentration of 30 wtppm and a trifluoromethanesulfonic acid ion concentration of 6.8 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 30.2 g (343 mmol) of tertiary amyl alcohol $C_5H_{12}O$ from the dropping funnel in dropwise manner by spending 1 hr. After the dropping, the temperature was increased to 20° C. with stirring for 1 hr. This reaction solution was distilled under a condition of 125° C. and 0.4 kPa, thereby obtaining 21.4 g of a fraction. The obtained fraction was found by $^1HNMR$ to be hafnium tetra-tertiary-amyloxide $Hf(C_5H_{11}O)_4$. It was found by an ICP atomic emission spectrometer that zirconium concentration of the fraction was 18 wtppm. Yield from the initial tetrakis(diethylamido)hafnium (zirconium concentration: 1,000 wtppm) was 39 wt %.

EXAMPLE 12

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by cooling to 0° C. and then adding 15.6 g (104 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 66.5 g of a fraction. The obtained fraction was found by $^1$HNMR to contain tetrakis(diethylamido)hafnium Hf[N($C_2H_5$)$_2$]$_4$ as a main component. It was found by an ICP atomic emission spectrometer that zirconium concentration of the fraction was 138 wtppm. It was found by ion chromatography that trifluoromethanesulfonic acid ion concentration of the fraction was 2.1 wt %. A bottom residue after the distillation was in 35.0 g and had a zirconium concentration of 1,884 wtppm and a trifluoromethanesulfonic acid ion concentration of 29.0 wt %.

Then, 65 g of the obtained fraction was put into a 500 mL, five-necked, glass flask equipped with a dropping funnel, a reflux condenser, a thermometer and a stirrer, followed by cooling to 0° C. and then adding 10.1 g (67 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.3 g of a fraction. The obtained fraction was found by $^1$HNMR to contain tetrakis(diethylamido)hafnium Hf[N($C_2H_5$)$_2$]$_4$ as a main component. It was found by an ICP atomic emission spectrometer that zirconium concentration of the fraction was 19 wtppm. It was found by ion chromatography that trifluoromethanesulfonic acid ion concentration of the fraction was 2.0 wt %. A bottom residue after the distillation was in 22.8 g and had a zirconium concentration of 355 wtppm and a trifluoromethanesulfonic acid ion concentration of 45.1 wt %.

Then, 40.0 g of the obtained fraction was put into a 500 mL, five-necked, glass flask equipped with a reflux condenser, a thermometer and a stirrer, followed by adding 1.0 g (13 mmol) of lithium diethylamide LiN($C_2H_5$)$_2$ and then stirring at 25° C. for 1 hr. Then, this reaction solution was distilled under a condition of 125° C. and 0.12 kPa, thereby obtaining 38.1 g of a fraction. The obtained fraction was found by $^1$HNMR to be tetrakis(diethylamido)hafnium Hf[N($C_2H_5$)$_2$]$_4$. Zirconium concentration of the fraction was 16 wtppm, and trifluoromethanesulfonic acid ion concentration of the fraction was less than 10 wtppm (detection limit). A bottom residue after the distillation was in 1.7 g and had a zirconium concentration of 30 wtppm and a trifluoromethanesulfonic acid ion concentration of 6.8 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 35.0 g (343 mmol) of 3-methyl-3-pentanol $C_6H_{14}O$ from the dropping funnel in dropwise manner by spending 1 hr. After the dropping, the temperature was increased to 20° C. with stirring for 1 hr. This reaction solution was distilled under a condition of 130° C. and 0.13 kPa, thereby obtaining 23.7 g of a fraction. The obtained fraction was found by $^1$HNMR to be tetrakis(3-methyl-3-pentoxy)hafnium Hf($C_6H_{13}O$)$_4$. It was found by an ICP atomic emission spectrometer that zirconium concentration of the fraction was 20 wtppm. Yield from the initial tetrakis(diethylamido)hafnium (zirconium concentration: 1,000 wtppm) was 39 wt %.

EXAMPLE 13

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium Hf[N($C_2H_5$)$_2$]$_4$ containing 1,000 wtppm of zirconium, followed by cooling to 0° C. and then adding 15.6 g (104 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 66.5 g of a fraction. The obtained fraction was found by $^1$HNMR to contain tetrakis(diethylamido)hafnium Hf[N($C_2H_5$)$_2$]$_4$ as a main component. It was found by an ICP atomic emission spectrometer that zirconium concentration of the fraction was 138 wtppm. It was found by ion chromatography that trifluoromethanesulfonic acid ion concentration of the fraction was 2.1 wt %. A bottom residue after the distillation was in 35.0 g and had a zirconium concentration of 1,884 wtppm and a trifluoromethanesulfonic acid ion concentration of 29.0 wt %.

Then, 65 g of the obtained fraction was put into a 500 mL, five-necked, glass flask equipped with a dropping funnel, a reflux condenser, a thermometer and a stirrer, followed by cooling to 0° C. and then adding 10.1 g (67 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 125° C. and 0.12 kPa, thereby obtaining 43.3 g of a fraction. The obtained fraction was found by $^1$HNMR to contain tetrakis(diethylamido)hafnium Hf[N($C_2H_5$)$_2$]$_4$ as a main component. It was found by an ICP atomic emission spectrometer that zirconium concentration of the fraction was 19 wtppm. It was found by ion chromatography that trifluoromethanesulfonic acid ion concentration of the fraction was 2.0 wt %. A bottom residue after the distillation was in 22.8 g and had a zirconium concentration of 355 wtppm and a trifluoromethanesulfonic acid ion concentration of 45.1 wt %.

Then, 40.0 g of the obtained fraction was put into a 500 mL, five-necked, glass flask equipped with a reflux condenser, a thermometer and a stirrer, followed by adding 1.0 g (13 mmol) of lithium diethylamide LiN($C_2H_5$)$_2$ and then stirring at 25° C. for 1 hr. Then, this reaction solution was distilled under a condition of 125° C. and 0.12 kPa, thereby obtaining 38.1 g of a fraction. The obtained fraction was found by $^1$HNMR to be tetrakis(diethylamido)hafnium Hf[N($C_2H_5$)$_2$]$_4$. Zirconium concentration of the fraction was 16 wtppm, and trifluoromethanesulfonic acid ion concentration of the fraction was less than 10 wtppm (detection limit). A bottom residue after the distillation was in 1.7 g and had a zirconium concentration of 30 wtppm and a trifluoromethanesulfonic acid ion concentration of 6.8 wt %.

Then, 20.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 71.3 g (343 mmol) of hexafluoroacetylacetone $C_5F_6H_2O_2$ from the dropping funnel in dropwise manner by spending 1 hr. After the dropping, the temperature was increased to 20° C. with stirring for 1 hr. This reaction solution was distilled under a condition of 120° C. and 13.3 Pa, thereby obtaining 40.9 g of a fraction. The obtained fraction was found by $^1$HNMR to be tetrakis(hexafluoroacetylacetonato)hafnium Hf($C_5F_6HO_2$)$_4$. It was found by an ICP atomic emission spectrometer that zirconium concentration of the fraction was 34 wtppm. Yield from the initial tetrakis(diethylamido)hafnium (zirconium concentration: 1,000 wtppm) was 39 wt %.

COMPARATIVE EXAMPLE 1

This comparative example was conducted similar to Example 1, but trifluoromethanesulfonic acid was not added, as described in the following.

A 500 mL, five-necked, glass flask was equipped with a dropping funnel, a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by conducting a distillation under a condition of 125° C. and 0.12 kPa, thereby obtaining 98 g of a fraction. The obtained fraction was found by $^1$HNMR to be tetrakis(diethylamido)hafnium $Hf[N(C_2H_5)_2]_4$. It was found by an ICP atomic emission spectrometer that zirconium concentration of the fraction was 950 wtppm.

Then, 95.0 g of the obtained fraction was put into a 500 mL, five-necked, glass flask equipped with a reflux condenser, a thermometer and a stirrer, followed by adding 1.5 g (19 mmol) of lithium diethylamide $LiN(C_2H_5)_2$ and then stirring at 25° C. for 1 hr. Then, this reaction solution was distilled under a condition of 125° C. and 0.12 kPa, thereby obtaining 94.9 g of a fraction. The obtained fraction was found by $^1$HNMR to be tetrakis(diethylamido)hafnium $Hf[N(C_2H_5)_2]_4$. Zirconium concentration of the fraction was 950 wtppm.

Then, 90.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 114.2 g (1,543 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 89.1 g of a fraction. The obtained fraction was found by $^1$HNMR to be hafnium tetra-tertiary-butoxide $Hf(C_4H_9O)_4$. It was found by an ICP atomic emission spectrometer that zirconium concentration of the fraction was 948 wtppm.

COMPARATIVE EXAMPLE 2

A 500 mL, five-necked, glass flask was equipped with a reflux condenser, a thermometer and a stirrer, followed by replacing the inside atmosphere of the flask with nitrogen. This flask was charged with 100.0 g (214 mmol) of a tetrakis(diethylamido)hafnium $Hf[N(C_2H_5)_2]_4$ containing 1,000 wtppm of zirconium, followed by adding 1.5 g (19 mmol) of lithium diethylamide $LiN(C_2H_5)_2$ and then stirring at 25° C. for 1 hr. Then, this reaction solution was distilled under a condition of 125° C. and 0.12 kPa, thereby obtaining 100.0 g of a fraction. The obtained fraction was found by $^1$HNMR to be tetrakis(diethylamido)hafnium $Hf[N(C_2H_5)_2]_4$. Zirconium concentration of the fraction was 985 wtppm.

Then, 95.0 g of the obtained fraction (tetrakis(diethylamido)hafnium) was put into a 500 mL, five-necked, glass flask equipped with a dropping funnel, a reflux condenser, a thermometer and a stirrer, followed by cooling to 0° C. and then adding 120.6 g (1,629 mmol) of tertiary butanol $C_4H_{10}O$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 94.1 g of a fraction. The obtained fraction was found by $^1$HNMR to be hafnium tetra-tertiary-butoxide $Hf(C_4H_9O)_4$. It was found by an ICP atomic emission spectrometer that zirconium concentration of the fraction was 983 wtppm.

90.0 g of the obtained hafnium tetra-tertiary-butoxide $Hf(C_4H_9O)_4$ was put into a 500 mL, five-necked, glass flask equipped with a reflux condenser, a thermometer and a stirrer, followed by cooling to 0° C. and then adding 3.2 g (21.3 mmol) of trifluoromethanesulfonic acid $CF_3SO_3H$ from the dropping funnel in dropwise manner by spending 1 hr. After the dropping, the temperature was increased to 20° C. with stirring for 1 hr.

This reaction solution was distilled under a condition of 78° C. and 0.11 kPa, thereby obtaining 66.2 g of a fraction. The obtained fraction was found by $^1$HNMR to contain hafnium tetra-tertiary-butoxide $Hf(C_4H_9O)_4$ as a main component. It was found by an ICP atomic emission spectrometer that zirconium concentration of the fraction was 980 wtppm.

The entire contents of Japanese Patent Application No. 2007-167635 (filed Jun. 26, 2007), of which priority is claimed in the present application, are incorporated herein by reference.

What is claimed is:

1. A process for producing hafnium tetra-tertiary-butoxide $Hf(OC_4H_9)_4$, comprising the steps of:
   (a) adding a compound containing a carbonyl or sulfonyl group, the compound being represented by the formula of $A(O_yXO_nRf)_m$,
   wherein A is a hydrogen, oxygen, or hafnium atom,
   X is a carbon or sulfur atom when A is a hydrogen atom or oxygen atom,
   X is a sulfur atom when A is a hafnium atom,
   each of m, n and y is 1, when A is a hydrogen atom and X is a carbon atom,
   m, n and y are respectively 1, 2 and 1, when A is a hydrogen atom and X is a sulfur atom,
   m, n and y are respectively 2, 1 and 0, when A is an oxygen atom and X is a carbon atom,
   m, n and y are respectively 2, 2 and 0, when A is an oxygen atom and X is a sulfur atom,
   m, n and y are respectively 4, 2 and 1, when A is a hafnium atom,
   Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom,
   Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;
   (b) subjecting a product of the step (a) to a distillation under reduced pressure, thereby removing the zirconium component from the crude hafnium amide;
   (c) adding a lithium alkylamide represented by the formula of $Li(NR_3R_4)$, where each of $R_3$ and $R_4$ independently represents a methyl or ethyl group, to a fraction obtained by the step (b);
   (d) subjecting a product of the step (c) to a distillation under reduced pressure;
   (e) adding tertiary butanol $C_4H_{10}O$ to a fraction obtained by the step (d); and
   (f) subjecting a product of the step (e) to a distillation under reduced pressure.

2. A process for producing tetrakis(acetylacetonato) hafnium $Hf(C_5H_7O_2)_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding acetylacetone $C_5H_8O_2$ to a fraction obtained by the step (d); and (f) subjecting a product of the step (e) to a distillation under reduced pressure.

3. A process for producing tetrakis(1-methoxy-2-methyl-2-propanolato)hafnium $Hf(C_5H_{11}O_2)_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding 1-methoxy-2-methyl-2-propanol $C_5H_{12}O_2$ to a fraction obtained by the step (d); and (f) subjecting a product of the step (e) to a distillation under reduced pressure.

4. A process for producing hafnium tetra-tertiary-amyloxide $Hf(OC_5H_{11})_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding tertiary amyl alcohol $C_5H_{12}O$ to a fraction obtained by the step (d); and (f) subjecting a product of the step (e) to a distillation under reduced pressure.

5. A process for producing tetrakis(3-methyl-3-pentoxy)hafnium $Hf(OC_6H_{13})_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding 3-methyl-3-pentanol $C_6H_{14}O$ to a fraction obtained by the step (d); and (f) subjecting a product of the step (e) to a distillation under reduced pressure.

6. A process for producing tetrakis(hexafluoroacetylacetonato)hafnium $Hf(C_5F_6HO_2)_4$, comprising the steps of:

(a) adding a compound containing a carbonyl or sulfonyl group, the compound being represented by the formula of $A(O_yXO_nRf)_m$, wherein A is a hydrogen, oxygen, or hafnium atom, X is a carbon or sulfur atom when A is a hydrogen atom or oxygen atom, X is a sulfur atom when A is a hafnium atom, each of m, n and y is 1, when A is a hydrogen atom and X is a carbon atom, m, n and y are respectively 1, 2 and 1, when A is a hydrogen atom and X is a sulfur atom, m, n and y are respectively 2, 1 and 0, when A is an oxygen atom and X is a carbon atom, m, n and y are respectively 2, 2 and 0, when A is an oxygen atom and X is a sulfur atom, m, n and y are respectively 4, 2 and 1, when A is a hafnium atom, Rf is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A is a hydrogen atom or oxygen atom, Rf is a $C_1$-$C_{12}$ perfluoroalkyl group when A is a hafnium atom, to a crude hafnium amide which is represented by the formula of $Hf[N(R_1)(R_2)]_4$, where each of $R_1$ and $R_2$ independently represents a methyl or ethyl group, and which contains a zirconium component as an impurity;

(b) subjecting a product of the step (a) to a distillation under reduced pressure, thereby removing the zirconium component from the crude hafnium amide;

(c) adding a lithium alkylamide represented by the formula of $Li(NR_3R_4)$, where each of $R_3$ and $R_4$ independently represents a methyl or ethyl group, to a fraction obtained by the step (b);

(d) subjecting a product of the step (c) to a distillation under reduced pressure;

(e) adding hexafluoroacetylacetone $C_5F_6H_2O_2$ to a fraction obtained by the step (d); and (f) subjecting a product of the step (e) to a distillation under reduced pressure.

7. A process according to claim 1, wherein, prior to conducting the step (c), the step (a) is repeated by adding the compound to the fraction obtained by the step (b).

8. A process according to claim 1, wherein the crude hafnium amide of the step (a) is tetrakis(diethylamido) hafnium.

9. A process according to claim 1, wherein the compound of the step (a) is one selected from the group consisting of acetic acid, trifluoroacetic acid, benzoic acid, methanesulfonic acid, trifluoromethanesulfonic acid, benzenesulfonic acid, acetic anhydride, trifluoroacetic anhydride, benzoic anhydride, methanesulfonic anhydride, trifluoromethanesulfonic anhydride, benzenesulfonic anhydride, and hafnium trifluoromethanesulfonato.

10. A process according to claim 1, wherein the compound of the step (a) is one selected from the group consisting of trifluoromethanesulfonic acid, hafnium trifluoromethanesulfonato, trifluoromethanesulfonic anhydride, trifluoroacetic acid, methanesulfonic acid, benzenesulfonic acid, and methanesulfonic anhydride.

11. A process according to claim 1, wherein the compound of the step (a) is trifluoromethanesulfonic acid.

12. A process according to claim 1, wherein an alkyl substituent of the lithium alkylamide of the step (c), which is represented by the formula of $R_3R_4$, is identical with an alkyl substituent of the hafnium amide of the step (a), which is represented by the formula of $(R_1)(R_2)$.

* * * * *